United States Patent
Detwiler et al.

(10) Patent No.: US 6,348,193 B1
(45) Date of Patent: Feb. 19, 2002

(54) METHOD FOR INHIBITING PATHOGENIC FUNGI AND BACTERIA IN PLANTS USING *PSEUDOMONAS AUREOFACIENS*

(75) Inventors: Alvin Ronald Detwiler, Haslett; Joseph M. Vargas, Jr., East Lansing; Nancy M. Dykema, Holt; Muraleedharan G. Nair, Okemos, all of MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 09/388,864

(22) Filed: Sep. 2, 1999

(51) Int. Cl.[7] .............................................. A01N 63/00
(52) U.S. Cl. .................................. 424/93.47; 435/253.3
(58) Field of Search ..................... 435/253.3; 424/93.47

(56) References Cited

U.S. PATENT DOCUMENTS 5,288,633 A * 2/1994 Cartwright ............... 435/253.3
5,658,794 A * 8/1997 Nair ......................... 435/253.3

OTHER PUBLICATIONS

Haynes et al. Pseudomonas aureofaciens Kluyver and phenazine alpha–carboxylic acid, its characteristics pigment. J. of Bacteriology, 1956. vol. 72. pp. 412–417.*

Cook et al., Biological and Cultural tests for control of plant diseases. 1988. vol. 3, p. 53.*

Weller D.M. Annual Review of Phytophathology, 1988, vol. 263 pp. 379–407. See entire document, especially p. 396, paragraph 1.*

* cited by examiner

*Primary Examiner*—Irene Marx
(74) *Attorney, Agent, or Firm*—Ian C. McLeod

(57) ABSTRACT

A method for controlling bacterial fungal diseases using *Pseudomonas aureofaciens* in admixture with metabolites, particularly phenazine-1-carboxylic acid (PCA) is described. *Pseudomonas aureofaciens* is particularly useful in inhibiting the microorganisms in cultivated dicot plants, cereal crops and nursery stock and seeds. The method is environmentally safe and economical.

13 Claims, No Drawings

METHOD FOR INHIBITING PATHOGENIC FUNGI AND BACTERIA IN PLANTS USING *PSEUDOMONAS AUREOFACIENS*

GOVERNMENT FUNDING

None

CROSS-REFERENCE TO RELATED APPLICATIONS

None

BACKGROUND OF THE INVENTION (1). Field of the Invention

The present invention relates to a method for controlling bacterial and fungal diseases in plants using *Pseudomonas aureofaciens* in admixture with its metabolites from growth of the *Pseudomonas aureofaciens*. In particular, the present invention relates to a novel strain of *Pseudomonas aureofaciens* which is useful in the method.

(2). Description of Related Art

Development of new chemical bacteriocides, and fungicides generally occurs through the mass screening of novel synthetic compounds. Utilization of antifungal compounds produced by microbial organisms, such as antibiotics, have been highly exploited in the development of medicinal compounds. Application of medicinal antibiotics for the management of plant diseases has been restricted due to concerns of the development of resistance to these compounds by potential human pathogens.

Several bacteria have been identified as producing a variety of classes of compounds that are antifungal in nature, including enzymes, siderophores, hydrogen cyanide, ethylene, and antibiotics. Although all of these compounds have been implicated in biological control activity by bacteria, the commercial application of enzymes for plant disease management is not likely due to their sensitivity to environmental conditions. Another class of compounds that would not be feasible for study are volatile compounds such as hydrogen cyanide and ethylene.

The use of bacteria as biological control agents is one of the fastest growing fields of research in disease management. The concept of the management of disease through the application of soilborne bacteria is attractive due to its sensitivity to environmental concerns. However, significant breakthroughs yielding biological controls that provide consistent disease management have not yet been realized.

*Pseudomonas aureofaciens* is a gram negative, rod-shaped bacterium possessing one or more flagella, is strictly aerobic, and chemoorganotrophic. *P. aureofaciens* is included in the class of fluorescent pseudomonads and was included taxonomically as a biovar of *Pseudomonas fluorescens* by Stanier et al (Journal of General Microbiology 43:159–271 (1966)). Inclusion of *P. aureofaciens* in the group of fluorescent pseudomonads is based on the ability of most strains to produce the fluorescent pigment pyoveridin. The name "*aureofaciens*" literally means to "make golden" which refers to its ability to turn artificial media to an orange-gold color. This color is caused by production of non-fluorescent phenazine pigments. Phenazine pigments reported to be produced by *P. aureofaciens* are phenazine-1-carboxylic acid (PCA), phenazine 2-oxophenazine and 2-oxophenazine-1-carboxylic acid (Trutko, S. M., et al., Biokhimima 54:1329–1336 (1990)). Evidence has been presented that the role of phenazine compounds produced by *P. aureofaciens* allows for the removal of excess reducing equivalents from NADH and NADPH under substrate and/or oxygen limitations.

The role of microflora in relation to the reduction of disease severity was brought to light with the identification of "suppressive soils". "Suppressive soils" refers to soils which reduce the level of disease intensity to a particular pathogen (Rovira, A. D., et al., The nature and mechanism of suppression. Pages 385–415 in: Biology and Control of Take-All, M. J. C. Asher and P. J. Shipton, eds. Academic Press, New York, N.Y., 538 pp. (1981)). Suppressive soils may be divided into two classes; general antagonism and specific antagonism (Gerlagh, M., Netherlands Journal of Plant Pathology 74:1–97 (1968)).

General antagonism may be found to some degree in all soils and can be directly related to high soil bacteria populations (Rovira, A. D., et al., The nature and mechanism of suppression. Pages 385–415 in: Biology and Control of Take-All, M. J. C. Asher and P. J. Shipton, eds. Academic Press, New York, N.Y., 538 pp. (1981)). Characteristics common to this type of antagonism include the maintenance of soil suppressiveness after heating to 70° C. for 30 minutes, inability for transfer to other soils, and the exhibition of greater suppression in undisturbed soils. It is fostered by the addition of organic amendments, increased suppression in soil at temperatures above 25° C., and is promoted by the use of ammonium-nitrogen ($NH_4^+$—N) rather than nitrate-nitrogen ($NO_{3-}$—N) (Cook, R. J., et al., Biological and cultural tests for control of plant diseases. 3:53 (1988)). Smith (Smith, A. M., Soil Biology and Biochemistry 8:293–298 (1976)) suggested that ethylene ($C_2H_4$) biosynthesis by soil microflora may be a major factor involved in general antagonism. Factors supporting the role of ethylene in general antagonism are that ethylene production in soil increases as soil temperatures increase up to 35° C., is promoted by ammonium-nitrogen but inhibited by nitrate-nitrogen, is fostered by the addition of organic amendments, and is greater in undisturbed bulk soils. Ethylene has also been shown to be inhibitory to *G. graminis* var. tritici at concentrations less than 5 parts-per-million in the soil atmosphere (Rovira, A. D., et al., The nature and mechanism of suppression. Pages 385–415 in: Biology and Control of Take-All, M. J. C. Asher and P. J. Shipton, eds. Academic Press, New York, NY, 538 pp. (1981)).

Specific antagonism occurs through continuous monoculture of a crop in the presence of a pathogen (Gerlagh, M., Netherlands Journal of Plant Pathology 74:1–97 (1968)). This results from the buildup of specific antagonistic microbial populations that are antagonistic to the pathogen. This type of antagonism occurs in soils of lower temperature than general antagonism (15–25° C.), is eliminated by 60° C. moist heat, can be transferred to other soils by mixing, and is related to the build-up of specific bacteria in the rhizosphere (Cook, R. J., et al., Biological and cultural tests for control of plant diseases. 3:53 (1988)).

One of the most studied models of suppressive soils involves take-all disease of wheat and other grasses as caused by the fungus *G. graminis*. General antagonism to this disease involves all of the factors previously listed. Research interest has been focused on the phenomenon known as "take-all decline" which is a form of specific antagonism in which "suppression (of take-all) develops with 2 or 3 years of wheat monoculture and severe take-all; the soil becomes "immune" to subsequent outbreaks of take-all if cropped exclusively thereafter to wheat and barley" (Cook, R. J., et al., Biological and cultural tests for control of plant diseases. 3:53 (1988)). This occurrence was first reported by Glynne (Glynne, M. D., Annals of Applied Biology 22:225–235 (1935)) in 1935, who noted a reduction in take-all severity after 4 consecutive wheat crops.

Several studies in the mid 1970's correlated fluorescent pseudomonads with the occurrence of take-all decline. Evaluation of 100 bacterial strains for specific antagonism to *G. graminis* var. tritici in greenhouse conditions by Cook and Rovira (Cook, R. J., et al., Biological and cultural tests for control of plant diseases. 3:53 (1988)), identified eight (8) strains which yielded suppression greater than or equal to those of natural suppressive soils. All eight strains were Pseudomonas spp., seven of which were fluorescent. Further evaluation of bacterial populations by Cook and Rovira (Cook, R. J., et al., Biological and cultural tests for control of plant diseases. 3:53 (1988)) indicated suppressive soils contained 1000 times more fluorescent pseudomonads than non-suppressive soils. Simon and Ridge (Simon, A., et al., Journal of Applied Bacteriology 37:459–460 (1974)) similarly found 100 to 1000 fold increases of fluorescent pseudomonads on infected root tissues than on healthy roots. Agar plate tests demonstrated that over 70% of the fluorescent pseudomonads isolated from suppressive soils were antagonistic to *G. graminis*. Increases in fluorescent pseudomonad populations have also been linked with the decline of take-all (*Gaeumannomyces graminis* var. avenae) of turfgrass (Sarniguet, A., et al., Plant and Soil 145:11–15 (1992)). Species of fluorescent pseudomonads that are correlated to the development of soil suppressiveness are *P. fluorescens* (Weller, D. M., et al., Phytopathology 73:463–469 (1983)) and *P. aureofaciens* (Cook, R. J., et al., Biological and Cultural tests for control of plant diseases. 3:53 (1988)).

Several mechanisms of pathogen suppression by fluorescent pseudomonads have been proposed. Competition for nutrients and colonization sites has not received recent attention but plays an important role in disease suppression. Bacteria which are capable of using a broad array of nutrients rapidly can reduce carbon and nitrogen sources available for pathogen sporulation and colonization (Weller, D. M., Annual Review of Plant Pathology 26:379–407 (1988)). Coupled with high metabolism is the ability to undergo rapid reproduction which increases the organism's potential for dispersal and occupation of available niches (Campbell, R., Biological control of microbial plant pathogens Cambridge University Press (1989)). Pseudomonas spp. act in this manner as exemplified by their non-fastidious nature (Palleroni, N. J., Pseudomonadaceae. pages 141–219 in:Bergey's Manual of Systematic Bacteriology, Volume 1, Kreig, N. R. and Holt, J. J., eds. Williams and Wilkins, Baltimore, Md. 1024 pp. (1984)).

The argument for disease suppression by competition emphasizes the importance of colonization in the development of specific antagonistic disease suppression. The degree to which *P. fluorescens* is able to colonize wheat root tissue can be directly correlated with a reduction in the number of root lesions caused by *G. graminis* var. tritici (Bull, C. T., et al., Phytopathology 81:954–959 (1991)). Colonization of plant roots by bacteria may be divided into two stages (Howie, W. J., et al., Phytopathology 77:286–292 (1987)). Stage I involves the ability of the bacterium to become attached to the plant root. Stage II is dependent on the bacterium's ability to compete for available nutrients. The ability of a bacterium to colonize root tissue is referred to as its competence. Several traits which may play a role in determining a bacterium's rhizosphere competence include surface polysaccharides, presence of flagella and/or fimbriae, chemotaxis, osmotolerance, and the ability to utilize complex carbohydrates (Weller, D. M., Annual Review of Plant Pathology 26:379–407 (1988)).

Siderophores were the first class of metabolic compounds associated with disease suppression by fluorescent pseudomonads (Kloepper, J. W., et al., Current Microbiology 4:317–320 (1980)). Siderophores are "low molecular weight, high affinity iron (III) chelators" (Weller, D. M., Annual Review of Plant Pathology 26:379–407 (1988)). Under conditions of low iron concentrations, these yellow-green fluorescent compounds are excreted by bacteria and complex with available iron. The bacterium is able to recognize and absorb this complex through membrane receptor proteins. It is believed that siderophores sequester iron thereby making it unaccessible to pathogenic fungi. Support for this mode of antagonism has come from studies in which mutants deficient in siderophore production are less suppressive than the siderophore producing parents (Becker, O., et al., Phytopathology 78:778–784 (1988)). Additional evidence has come from studies indicating that the addition of the synthetic iron chelating compound iron ethylenediamine-di-O-hydroxyphenylacetic acid (Fe-EDDA) yields disease suppression. Addition of excess iron in the form of ferric-ethylenediaminetetraacetic acid (Fe-EDTA) represses siderophore production and eliminates suppressiveness (Weller, D. M., et al., Phytopathology 78:1094–1100 (1988)). Antibiosis by siderophore activity has been linked to antagonism toward Pythium spp. (Becker, O., et al., Phytopathology 78:778–784 (1988)), *Fusarium oxysporum* (Elad, Y., et al., Phytopathology 75:1053–1059 (1985)), and *G. graminis* var. tritici (Kloepper, J. W., et al., Current Microbiology 4:317–320 (1980)). Recent work by Hamdan et al., (Hamdan, H., The fluorescent siderophore of *Pseudomonas fluorescens*: role in suppression of *Gaeumannomyces graminis* var. tritici and genetic analysis of siderophore production. PhD thesis, Washington State University, Pullman (1988)) involving the generation of siderophore deficient mutants indicates that siderophores have no significant effect on take-all caused by *G. graminis* var. tritici. Although the role of siderophores in the suppression of *G. graminis* var. tritici is still in contention, there is little argument regarding it's role in the suppression of Pythium spp. in soil.

Disease suppression of soil pathogens by Pseudomonas spp. has been strongly attributed to the production of antibiotics. Two antibiotics have been attributed to the inhibitory nature of fluorescent pseudomonads, 2,4-diacetylphloroglucinol (DAPG) (Shanahan, P., et al., Applied and Environmental Microbiology 58:353–358 (1992)) and phenazine-1-carboxylic acid (PCA) (Haygood, R. A., et al., Phytopathology 80:435 (1990)). Strain Q2-87 of *P. aureofaciens* which produces DAPG was identified as being suppressive of take-all. DAPG was later confirmed as being a source of antifungal activity of *P. aureofaciens* Q2-87 on *G. graminis* var. tritici (Vincent, M. N., et al., Applied and Environmental 57:2928–2934 (1991)).

The production of PCA by *P. aureofaciens* was first identified by Haynes et al., in 1956 (Haynes, W. C., et al., J. of Bacteriology 72:412–417 (1956)). Recent work (Gurusiddaiah, S., et al., Characterization of an antibiotic produced by a strain of *Pseudomonas fluorescens* inhibitory to *Gaeumannomyces graminis* var. tritici and Pythium spp. Antimicrobial Agents and Chemotherapy 29:488–495 (1986)) has identified PCA as playing a major role in the inhibitory activity of *P. fluorescens* against *G. graminis* var. tritici. Pure crystals of this compound are needle-shaped and yellow to green-yellow in color. PCA was shown to be inhibitory to a broad range of fungi with minimum inhibitory concentrations (MIC) to completely prevent fungal growth ranging from 1 to 40 μg/ml in in vitro tests (Gurusiddaiah, S., et al., Characterization of an antibiotic produced by a strain of *Pseudomonas fluorescens* inhibitory to *Gaeumannomyces graminis* var. tritici and Pythium spp. Antimicrobial Agents and Chemotherapy 29:488–495 (1986)). Initial reports of the structure of PCA by Gurusiddaiah et. al. (Gurusiddaiah, S., et. al., Characterization of an antibiotic produced by a strain of *Pseudomonas fluorescens* inhibitory to *Gaeumannomyces graminis* var. tritici and Pythium spp. Antimicrobial Agents and Chemotherapy 29:488–495 (1986)) proposed that PCA occurred as a dimeric molecule. However, this structure of the antibiotic was later revised by Brisbane et. al. (Brisbane, P. G., et. al., Antimicrobial Agents and Chemotherapy 31:1967–1971 (1987)), who showed that the antibiotic existed in a monomeric state rather than as a dimer.

Thomashow and Weller (Thomashow, L. S., et. al., Journal of Bacteriology 170:3499–3508 (1988)) demonstrated the importance of PCA in biological suppression of take-all by *P. fluorescens* 2–79 through the generation of mutants deficient in PCA production by transposon mutagenesis. All PCA deficient mutants were unable to inhibit *G. graminis* var. tritici in agar plate tests and provided significantly lower levels of disease suppression in greenhouse studies. Similar studies by Pierson and Thomashow (Pierson, L. S., et. al., Phytopathology 78:1522 (1988)) illustrated similar results with *P. aureofaciens* strain 30–84. Thomashow et. al (Thomashow, L. S., et. al., Applied and Environmental Microbiology 56:908–912 (1990)) were able to quantify the production of PCA by *P. aureofaciens* and *P. fluorescens* on wheat roots grown in steamed and natural soil in the greenhouse. Concentrations of PCA detected in the steamed and natural soils were up to 578 and 133 ng/g root, respectively. PCA was also recovered from the roots of seed treated plants grown in wheat fields (5–12 ng/g root) and in virgin fields (19–27 ng/g root). These results demonstrated the production of antibiotics in the environment and also confirmed that very small amounts of antibiotics delivered to the microsite by biological control agents can be effective in disease management.

The utilization of antibiotics produced by microorganisms such as Penicillium sp (penicillin), *Streptomyces griseus* (streptomycin), *Streptomyces erythraeus* (erythromycin), *Cephalosporium acremonium* (cephalosporin), and several others (Pelczar, M. J., Jr., et al., Microbiology. McGraw-Hill. New York, N.Y. 952 pp. (1977)) for medical uses have been well documented. The potential for application of antibiotics as chemical treatments for plant disease has recently been explored. Application of culture filtrates of Bacillus subtilis provided better management of bean rust than the fungicide mancozeb (Baker, C. J., et al., Plant Disease 69:770–772 (1985)) and protected peaches from infection by *Monilinia fructicola* (Pusey, P. L., et al., Plant Disease 68:753–756 (1984)). Melvin et al., (Melvin, P., et al., Hortscience 28:195–196 (1993)) demonstrated that application of the antibiotic faeriefungin produced by *Streptomyces griseus* var. autotrophicus provided management of summer patch disease of turfgrass caused by *Magnaporthe poae* equal to that of the chemical fungicide fenarimol.

U.S. Pat. Nos., 5,658,794 and 5,665,351 to Nair et al describe the application of *Pseudomonas aureofaciens* to turfgrass. The metabolites were removed from *Pseudomonas aureofaciens* as can be seen from Example 1 of the patent.

OBJECTS

It is therefore an object of the present invention to provide strains of *Pseudomonas aureofaciens* with its metabolites which inhibit bacteria and fungi. Further still, it is an object of the present invention to provide biological control of the bacteria and fungi in a manner which is environmentally safe and economical. These and other objects will become increasingly apparent by reference to the following description.

SUMMARY OF THE INVENTION

The present invention relates to a method for inhibiting fungi and bacteria present with a plant material which comprises: applying an effective amount of a mixture of a biologically pure culture of *Pseudomonas aureofaciens* and its metabolites in a growth medium for the culture containing the metabolites to the plant material so that the fungi and bacteria present with the plant material are inhibited. The plant material can harbor one or both of fungi or bacteria. These microorganisms are generally naturally present on an exposed surface of the plant material as a pathogen.

The present invention is based upon the fact that it has been discovered that concentrates of Pseudomonas aureofaciens, particularly ATCC 55670, can be maintained in active condition for application to the plant material in the presence of the metabolites which are antibiotics. Thus the concentrate composition can contain between about $10^5$ to $10^{12}$ cfu/gram or ml and about 0.1 to 100 mg/ml of the antibiotics, primarily PCA. The resulting composition can be diluted in water and applied to the plant material.

The plant material can be a monocot or a dicot or a conifer. The preferred plant materials are cultivated dicot plants, cereal crops, nursery stock and seeds. Monocots are one of the two major types of flowering plants are characterized by having a single cotyledon, floral organs arranged in threes or multiples of three, and parallel-veined leaves; and include grasses, cattails, lilies, and palm trees. One of the two major groups in the Angiosperms, monocots are characterized by having a single seed leaf (cotyledon), flower parts in 3's or multiples of 3, monoaperturate pollen (although some dicots also have this feature), parallel veins in their leaves, and scattered vascular bundles in their stems. Dicots are one of the two main types of flowering plants and are characterized by having two cotyledons, floral organs arranged in cycles of four or five, and leaves with reticulate veins. This includes trees and most ornamental and crop plants. Conifers are identified by having needles.

DESCRIPTION OF PREFERRED EMBODIMENTS

The strain *Pseudomonas aureofaciens* (Tx-1) is deposited as ATCC 55670 with the American Type Culture Collection, 10801 University Boulevard, Manassas, Va. 20110–2209. The deposit was made on Jul. 31, 1995 under the Budapest Treaty and is available upon request by name and ATCC number. Bacteria strain Tx-1 was isolated at Michigan State University, East Lansing, Mich., from the soil of a turfgrass sample. It was chosen due to the pronounced zone of inhibition surrounding the bacterial colony. The taxonomic disposition of Tx-1 was assessed by fatty acid analysis and by carbon utilization. Reference is also made to Bergey's Manual of Determinative Bacteriology, 9th Edition, for general identification characteristics of *Pseudomonas aureofaciens*. This strain is described in detail in U.S. Pat. Nos. 5,658,794 and 5,665,351 which are incorporated by reference herein.

*Pseudomonas aureofaciens* is preferably applied in an amount of $2 \times 10^5$ to $2 \times 10^7$ CFU per ml in solution along with its metabolites to the plant or seed.

EXAMPLE 1

The purpose of this Example was to screen various plant pathogens against Pseudomonas aureofaciens strain Tx-1 with metabolites in a plate bioassay in order to generally evaluate antifungal activity.

Pseudomonas aureofaciens strain Tx-1 (Tx-1) was grown in TSB for 48 hours at 30° C. One transfer loop full of bacteria was streaked down the center of each potato dextrose agar (PDA) plate. PCA was in the growth medium. The plates were incubated at 30° C. for 48 hours. Fungi studied in this screening were grown on PDA and included: *Sclerotinia homoeocarpa* (dollar spot), Pythium sp. (Pythium blight), *Rhizoctonia solani* (3 different isolates, 2 from peanut and 1 brown patch on turf), cold temperature Rhizoctonia cereal is sp. (yellow patch), *Laetisaria fuciformis* (red thread), *Colletotrichum graminicola* (turfgrass anthracnose), *Gaeumannomyces graminis* (take all patch), *Sclerotium rolfsii* (from peanut), *Phytophthora cinnamomi* (root rot of woody plants), Colletotrichum sp. (fern anthracnose), *Microdochium nivale* (Microdochium patch), and *Leptosphaeria korrae* (necrotic ring spot). Four 4 mm agar plugs containing mycelia of each fungal pathogen were transferred to 2 PDA plates without bacteria (control) and 2 with Tx-1. The agar plugs were placed 15 mm from the edge of the bacterial streak and were 30 mm apart in the control plates. Each plug represented 1 replication. Plates were incubated at 26° C. (room temperature). Fungal growth was measured in millimeters after 3, 6 and 10 days of incubation. Photographs were also taken periodically throughout the screening. Colony diameter was measured parallel to and perpendicular to the bacterial streak, and the average radius was calculated from these measurements. Colony area was calculated using $\pi r^2$, where r=average radius. Data were subjected to ANOVA2 and means separated using Tukey's test (p=0.05).

*S. homoeocarpa*: After 3 and 6 days of growth, Tx-1 with its metabolites provided significant inhibition of growth of *S. homoeocarpa* almost totally preventing any growth at all. Tx-1 provided more significant reduction in growth when compared to *Burkholderia cepacia* as well. *B. cepacia* did not provide significant control of *S. homoeocarpa* growth.

Rhizoctonia sp.: After 3 days of growth, Tx-1 with its metabolites provided significant inhibition of growth for the 3 *R. solani* isolates and the cold temperature Rhizoctonia sp. (CT-R. sp.). After 6 days of growth, Tx-1 showed significant growth inhibition of the Rs-HTRC, Rs-9020 and CT R. sp. when compared to the control plates. There was no significant difference between Tx-1 and the control for the Rs-903 isolate. After 10 days of growth, Tx-1 and its metabolites still provided inhibition of CT R. sp. There was no difference between Tx-1 and its metabolites and the control for Rs-HTRC, Rs-903, and Rs-9020.

Pythium sp., *C. graminicola* (turfgrass anthracnose). *L. korrae* and *M. nivale*: For each of these pathogens, Tx-1 and its metabolites showed growth inhibition when compared to both the control for the 3, 6 and 10 day measurements.

*G. graminis*: There was significant growth inhibition of *G. graminis* by Tx-1 and its metabolites when compared to control.

*L. fuciformis*: Tx-1 and its metabolites provided complete growth inhibition after 10 days.

*P. cinnamomi*: Tx-1 and its metabolites provided significant growth inhibition of the *P. cinnamomi* when compared to the control for all measurement dates.

Colletotrichum sp. (fern anthracnose): Tx-1 and its metabolites provided significant growth inhibition of the fern anthracnose fungus. By the day 10 measurement, Tx-1 was significantly still antagonistic and provided significant control.

*S. rolfsii*: Tx-1 and its metabolites completely inhibited growth of *S. rolfsii*. Measurements were not taken after six days of growth because the control was already full of fungal mycelia.

*P. aureofaciens* strain Tx-1 and its metabolites proved to be efficacious than against the pathogens screened in this bioassay except for the following pathogens which were the same statistically: *G. graminis*, Colletotrichum sp. (fern) (days 3 and 6 only), Rs (days 6 and 10), and *L. fuciformis* (day 10 only).

EXAMPLE 2

Pseudomonas aureofaciens strain Tx-1 with its metabolites was screened, in vitro, against a representative of each of the five plant pathogenic bacterial genera. Representatives of these 5 genera cause serious bacterial diseases of fruits and vegetables. An in vitro plate bioassay was conducted in which *P. aureofaciens* strain Tx-1 was screened for efficacy against strains of Pythium sp. and *Rhizoctonia solani* (turf and vegetable pathogens). *P. aureofaciens* strain Tx-1 was screened, in vitro, against *Sclerotium rolfsii* (peanuts), *Rhizoctonia solani* (peanuts), Phytophthora sp. (woody plants), and Colletotrichum sp. (fern). *P. aureofaciens* strain Tx-1 is effective against a broad range of fruit and vegetable fungal pathogens. The results are shown in Table 1.

TABLE 1

Bioassay Using *Pseudomonas aureofaciens* strain Tx-1
Average colony diameter (cm$^2$) of fungal growth.

| Pathogen | Host | Number of incubation days | *P. aureofaciens* Tx-1 | Control |
| --- | --- | --- | --- | --- |
| Rhizoctonia solani | Sugarbeets | 5 | 26.1 | 33.2 |
| Phytophthora sojae | Beans | 7 | 7.3 | 25.8 |
| Phomopsis sp. | Grapes | 7 | 3.5 | 25.0 |
| Botrytis cinerea | Strawberries | 7 | 13.9 | 33.3 |
| Monilinia sp. | Stone fruits, apples | 10 | 0.7 | 30.3 |
| Colletotrichum sp. | Blueberries | 1o | 12.6 | 24.8 |
| Phytophthora cinnamomi | Woody plants | 10 | 0.9 | 6.5 |

EXAMPLE 3

*P. aureofaciens* is fermented and applied directly to the fruit or vegetable crops at appropriate rates and timing intervals during production and storage in order to control target diseases.

EXAMPLE 4

Field and greenhouse trials are conducted to determine the efficacy and feasibility of managing fruit and vegetable diseases in the field and during postharvest storage. The mixture of Tx-1 and its metabolites is applied directly to the plants rather than to the soil.

It is intended that the foregoing description be only illustrative of the present invention and that the present invention be limited only by the hereinafter appended claims.

We claim:

1. A method for inhibiting pathogenic fungi and bacteria present on or around a plant material which is a dicot or conifer which comprises:

applying an effective amount of a mixture of a biologically pure culture of *Pseudomonas aureofaciens* strain deposited as ATCC 55670 and its active metabolites in the growth medium used to grow the strain wherein the mixture contains the strain, the growth medium, and the metabolites, to the plant material so that the pathogenic fungi and bacteria present with the plant material are inhibited, and wherein the plant is selected from the group consisting of fruit plants, vegetable plants, shrub plants, flower plants, bedding plants, tree plants, and nursery stock plants.

2. The method of claim 1 wherein the application to the plant material is to a fruit or vegetable and the application is before harvesting of the fruit or vegetable.

3. The method of claim 1 wherein the application to the plant material is to a fruit or vegetable and the application is after harvesting of the fruit or vegetable.

4. The method of claim 1 wherein the application to the plant material is to a shrub plant.

5. The method of claim 1 wherein the application to the plant material is to a flower.

6. The method of claim 1 wherein the application to the plant material is to a bedding plant.

7. The method of claim 1 wherein the application to the plant material is by spraying.

8. The method of claim 1 wherein the application to the plant material is to a tree.

9. The method of claim 1 wherein the application to the plant material is to nursery stock.

10. The method of claim 1 wherein the application to the plant material is to a seed.

11. The method of claim 1 wherein the application to the plant material is by a drip system which applies the mixture to a plant as the plant material.

12. The method of claim 1 wherein the application to the plant material is to the soil.

13. The method of claim 1 wherein the strain is present in an amount between $10^5$ and $10^{12}$ CFU per ml or gram.

* * * * *